(12) United States Patent
Bitter et al.

(10) Patent No.: US 8,158,945 B2
(45) Date of Patent: Apr. 17, 2012

(54) DETECTOR ARRANGEMENT FOR A NONDISPERSIVE INFRARED GAS ANALYZER AND METHOD FOR THE DETECTION OF A MEASURING GAS COMPONENT IN A GAS MIXTURE BY MEANS OF SUCH A GAS ANALYZER

(75) Inventors: Ralf Bitter, Karlsruhe (DE); Camiel Heffels, Stutensee-Büchig (DE); Thomas Hörner, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 71 days.

(21) Appl. No.: 12/598,488

(22) PCT Filed: Apr. 25, 2008

(86) PCT No.: PCT/EP2008/055100
§ 371 (c)(1),
(2), (4) Date: Nov. 2, 2009

(87) PCT Pub. No.: WO2008/135416
PCT Pub. Date: Nov. 13, 2008

(65) Prior Publication Data
US 2010/0134784 A1   Jun. 3, 2010

(30) Foreign Application Priority Data

May 2, 2007  (DE) .......................... 10 2007 020 596
Jul. 30, 2007 (DE) .......................... 10 2007 035 711

(51) Int. Cl.
*G01J 5/00* (2006.01)
(52) U.S. Cl. ................................. 250/339.13
(58) Field of Classification Search ............. 250/339.13, 250/343, 345; 356/51, 437
See application file for complete search history.

(56) References Cited

U.S. PATENT DOCUMENTS 2,924,713 A   2/1960  Liston
(Continued)

FOREIGN PATENT DOCUMENTS

DE   1 109 418 B   6/1961
(Continued)

OTHER PUBLICATIONS

Maris M. A. et al.: "Nonlinear Multicomponent Analysis by infrared Spectrophotometry", Analytical Chemistry; American Chemical Society; Columbus, US, No. 55, No. 11, Sep. 1, 1983, pp. 1694-1703, the whole document.

(Continued)

*Primary Examiner* — David Porta
*Assistant Examiner* — Marcus Taningco

(57) ABSTRACT

A detector arrangement for detection of a measuring gas component in a gas mixture is provided. The arrangement includes a gas analyzer, a first single-layer receiver and a further single-layer receiver, the first single-layer receiver containing the measuring gas component and the further single-layer receiver containing a transverse gas. A concentration of the measuring gas component in the gas mixture is determined from signals delivered by sensors of the single-layer receivers. An evaluating device includes an n-dimensional calibration matrix for obtaining matrix signal values. Signal values of different known concentrations of the measuring gas component in the presence of different known transverse gas concentrations are stored as n-tubules in the evaluating device. The concentration of the measuring gas component in the presence of unknown transverse gas concentrations is determined by comparing n-tuples of signal values thereby obtained with the n-tuples of signal values stored in the calibration matrix.

17 Claims, 2 Drawing Sheets

U.S. PATENT DOCUMENTS

| | | | |
|---|---|---|---|
| 3,560,736 A | * | 2/1971 | Billetdeaux et al. .......... 250/343 |
| 3,731,092 A | * | 5/1973 | Freilino ......................... 250/346 |
| 5,321,266 A | | 6/1994 | Weinel |
| 5,446,681 A | * | 8/1995 | Gethner et al. ................. 702/27 |
| 5,764,354 A | * | 6/1998 | Aidam et al. .............. 356/243.1 |
| 5,900,635 A | * | 5/1999 | Weckstrom ................... 250/345 |
| 6,552,793 B1 | | 4/2003 | Kastner |

FOREIGN PATENT DOCUMENTS

| | | |
|---|---|---|
| DE | 9014162 U1 | 12/1990 |
| DE | 195 18 322 C1 | 7/1996 |
| DE | 19949439 C1 | 2/2001 |
| JP | 09101259 A | 4/1997 |
| WO | WO 92/07326 A1 | 4/1992 |
| WO | WO 2005/078413 A1 | 8/2005 |

OTHER PUBLICATIONS

Thomas E. V. et al., "Comparison of Multivariate Calibration Methods for Quantitative Spectral Analysis", Analytical Chemistry, American Chemical Society, Columbus, US, No. 62, No. 10, May 15, 1990, pp. 1091-1099, the whole document.

J. Staab; "Industrielle Gasanalyse", Oldenbourg, 1994, pp. 167f and 172f.

* cited by examiner

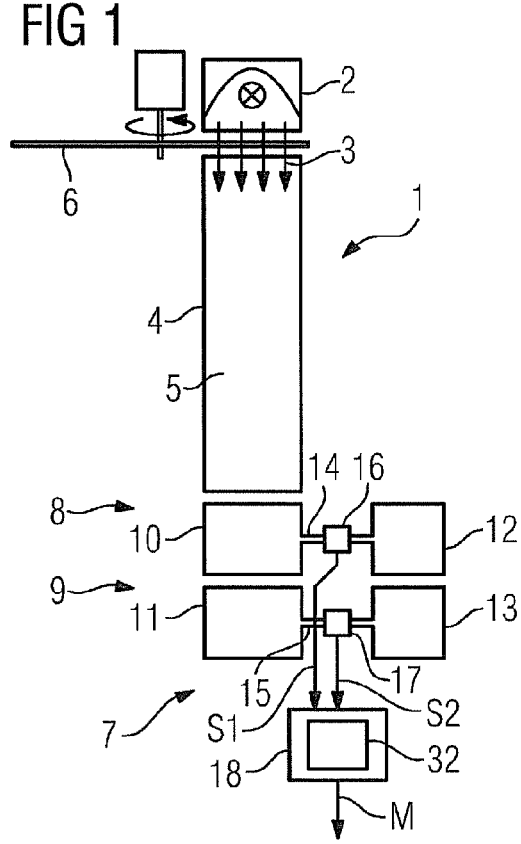
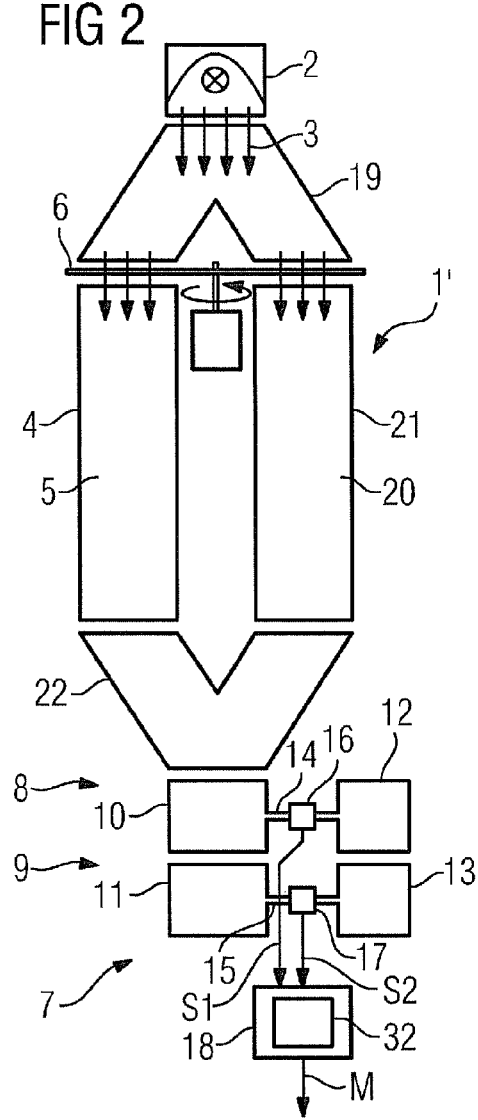

DETECTOR ARRANGEMENT FOR A NONDISPERSIVE INFRARED GAS ANALYZER AND METHOD FOR THE DETECTION OF A MEASURING GAS COMPONENT IN A GAS MIXTURE BY MEANS OF SUCH A GAS ANALYZER

CROSS REFERENCE TO RELATED APPLICATIONS

This application is the US National Stage of International Application No. PCT/EP2008/055100 filed Apr. 25, 2008, and claims the benefit thereof. The International Application claims the benefits of German Application No. 10 2007 020 596.3 DE filed May 2, 2007, and of German Application No. 10 2007 035 711.9 DE filed Jul. 30, 2007. All of the applications are incorporated by reference herein in their entirety.

FIELD OF INVENTION

The invention relates to a detector arrangement for a non-dispersive infrared (NDIR) gas analyzer for detecting a measuring gas component in a gas mixture, comprising a first single-layer receiver and at least one additional single-layer receiver which are located one behind the other in the beam path of the gas analyzer, the first single-layer receiver containing the measuring gas component or a gas spectrally overlaying the measuring gas component and the at least one additional single-layer receiver containing a transverse gas, the measuring gas component—also in a concentration different from that of the first single-layer receiver—or a gas spectrally overlaying the measuring gas component, and comprising an evaluating device for determining the concentration of measuring gas component in the gas mixture from signals supplied from, for example pressure- or flow-sensitive, sensors of the single-layer receivers.

The invention also relates to a method for detecting a measuring gas component in a gas mixture by means of a non-dispersive infrared (NDIR) gas analyzer.

BACKGROUND OF INVENTION

A gas analyzer of this kind, known from DE-AS 1 109 418, comprises a detector arrangement with two single-layer receivers located one behind the other, which are both filled with the measuring gas component, the partial pressure of the measuring gas component being selected so as to be lower in the first single-layer receiver than in the second single-layer receiver. Alternatively, the two single-layer receivers contain different gas fillings, wherein for example for measuring methane in the presence of water vapor the first single-layer receiver is filled with the measuring gas component methane and the second single-layer receiver is filled with ammonia as a replacement for the transverse gas water vapor. The single-layer receivers each comprise an active detector chamber located in the beam path of the gas analyzer and a passive equalizing chamber, outside of the beam path, connected to the detector chamber by a connecting line and which contains a membrane capacitor as the pressure-sensitive sensor. Alternatively a flow-sensitive sensor can be arranged in the connecting line, as is known for example from J. Staab: "Industrielle Gasanalyse" [Industrial Gas Analysis], Oldenbourg, 1994, pages 167f and 172f.

With the detector arrangement known from DE-AS 1 109 418 the signals supplied by the sensors of the two single-layer receivers are fed to an evaluation circuit which is constructed as a compensation circuit and forms the ratio of the two signals. Assuming that the gas filling of the second single-layer receiver is selected such that, in relation to composition and/or pressure, the absorption region of this second single-layer receiver largely overlaps the narrower absorption region of the first single-layer receiver, the sensor signal of the second single-layer receiver, which is based solely on the effect of the radiation not absorbed in the first single-layer receiver, and can therefore be attributed to the component of the broad absorption region, compensates the fraction in the sensor signal of the first single-layer receiver which originates precisely from this overlapping component of the broad absorption region in the first single-layer receiver.

SUMMARY OF INVENTION

An object of the invention is to compensate the effect of transverse gases on the measuring result without the above-stated precondition having to be fulfilled.

The object is achieved by a detector arrangement as claimed in the independent claim, wherein the evaluating device includes an n-dimensional calibration matrix corresponding to the number n of single-layer receivers and in which signal values from sensors obtained in the case of different known concentrations of measuring gas component in the presence of different known transverse gas concentrations are stored as n-tuples and the evaluating device is adapted to determine the concentration of the measuring gas component when measuring unknown concentrations of the measuring gas component in the presence of unknown transverse gas concentrations by comparing the n-tuples of signal values obtained thereby with the n-tuples of signal values stored in the calibration matrix.

The object is further achieved by a method as claimed in the independent claim.

Advantageous developments of the detector arrangement and the method are disclosed in the dependent claims.

In addition to the main signal fraction produced by the absorption of radiation in its own single-layer receiver, the sensor signal of each single-layer receiver also includes smaller signal fractions from the respective other single-layer receivers. The sensor signals of n single-layer receivers therefore form an n-dimensional result matrix. If the first single-layer receiver contains the measuring gas component and the downstream n−1 single-layer receivers are filled with different transverse gases, the concentration of a measuring gas component may also be determined in the presence of the transverse gases in different concentrations. According to the invention the signal values obtained with different known concentrations of measuring gas component in the presence of different known concentrations of the n−1 different transverse gases are firstly stored as n-tuples, together with the respective known concentration value of the measuring gas component, in a calibration matrix for this purpose. If an unknown concentration of measuring gas component is then to be subsequently determined in the presence of the transverse gases, whose concentrations are likewise unknown, the n-tuples of signal values obtained thereby are compared with the n-tuples of signal values stored in the calibration matrix and the corresponding concentration value of the measuring gas component determined from the calibration matrix.

If the at least one additional single-layer receiver is filled with a transverse gas then the concentration of the respective transverse gas component may also be determined by comparing the n-tuples of signal values obtained when measuring unknown concentrations of the measuring gas component in the presence of unknown transverse gas concentrations with the n-tuples of signal values stored in the calibration matrix.

A limited number of measurements with known concentrations of measuring gas component in the presence of known concentrations of the transverse gases is sufficient to create the calibration matrix and to obtain a series of basic values, starting from which the calibration matrix is completed by means of a simulation program, for example by interpolation of the basic values or extrapolation. Here the term calibration matrix also includes the describing mathematical functions and their parameters, for example using polynomials.

The general applicability of the invention is only limited by the dynamic ranges of the respective gases. In practice both the dynamic range of the measuring gas component and the dynamic ranges of the transverse gases must therefore be adapted to requirements by the appropriate design of the gas analyzer (radiator, length of the cells and detector chambers used).

As an alternative to filling the additional single-layer receivers with transverse gases they could also be filled with the measuring gas component. This can take place at different concentrations, with the concentration in the first single-layer receiver preferably being the lowest. In this case, rather than determining the transverse gases directly, as above, only their effect on the measurement of the concentration of the measuring gas component is determined. As a result transverse gas effects can be directly compensated with the required accuracy of the measuring gas component, without the dynamic ranges of the transverse gases having to be considered. Absorption in the first single-layer receiver produces a signal which contains information on the measuring gas component and the transverse gases present. One effect of absorption in the first single-layer receiver, however, is also that the various wavelength fractions of the radiation are weighted differently, the wavelength-dependent weighting corresponding to the transmission behavior of the measuring gas component. In the following single-layer receiver this wavelength-weighted radiation is now integrally detected again, so it is possible to distinguish between different spectral forms and therewith different concentrations of the transverse gases. In other words, an n-dimensional result matrix is also produced here which leads to an exact measuring gas concentration using the n obtained signal values respectively, and compensates the transverse gas effect.

As in real measuring situations the relevant transverse gases and the size of their concentrations are known, a corridor can be established in the calibration matrix starting from the expected transverse gas concentrations and their deviations. When measuring unknown concentrations of measuring gas component in the presence of the expected transverse gas concentrations an error can be signaled if the obtained n-tuples of signal values lie outside of the corridor.

The position of the n-tuples of signal values within the calibration matrix is generally dependent on different measuring and/or device-specific parameters, and, in addition to the above-stated concentrations of the measuring gas component and the expected transverse gas component, these also include other parameters, such as changes in the radiant power of the infrared radiator, contaminants in the radiation path, or the absorption properties of gases penetrating the measuring system unexpectedly, or even mechanical damage to the windows of the sample cell. The effect of such additional parameters may advantageously be determined in advance by varying them while keeping the remaining measuring and/or device-specific parameters constant, and the direction in which the n-tuples of the obtained signal values vary within the calibration matrix is determined in the process. Thus for example, while the transverse gas concentrations are kept constant the intensity of the radiation produced can be varied in order to determine the effect of changes in transmission, which are independent of wavelength, on the measuring result caused by ageing of the infrared radiator or contaminants in the sample cell. Similarly, while keeping the concentrations of certain transverse gases constant, the concentration of an additional transverse gas can be varied to determine its effect on the measuring result.

If a plurality of said parameters is effective simultaneously, then it is not easily possible to determine which parameter is responsible for changes in the position of the n-tuples obtained during measurement. As already stated above, starting from the expected transverse gas concentrations and their deviations, a corridor can, however, be established in the calibration matrix for real measuring situations outside of which the relevant transverse gases and their concentrations can be assumed to be non-disruptive. If therefore the n-tuples of signal values obtained during a measurement move out of the corridor, the number of parameters that can be regarded as the being responsible for the movement of the n-tuples reduces. By way of example, it can then be determined using the direction of movement of the n-tuples whether the cause thereof lies in a change in transmission, which is independent of wavelength (change in radiation intensity or contamination of the cells), or in the occurrence of an unexpected transverse gas.

BRIEF DESCRIPTION OF THE DRAWINGS

Reference will be made hereinafter to the drawings to describe the invention further. In detail:

FIG. 1 shows an exemplary embodiment of an NDIR gas analyzer in single-beam design, FIG. 2 shows an example of an NDIR gas analyzer in a two-beam design.

DETAILED DESCRIPTION OF INVENTION

Figure 3:
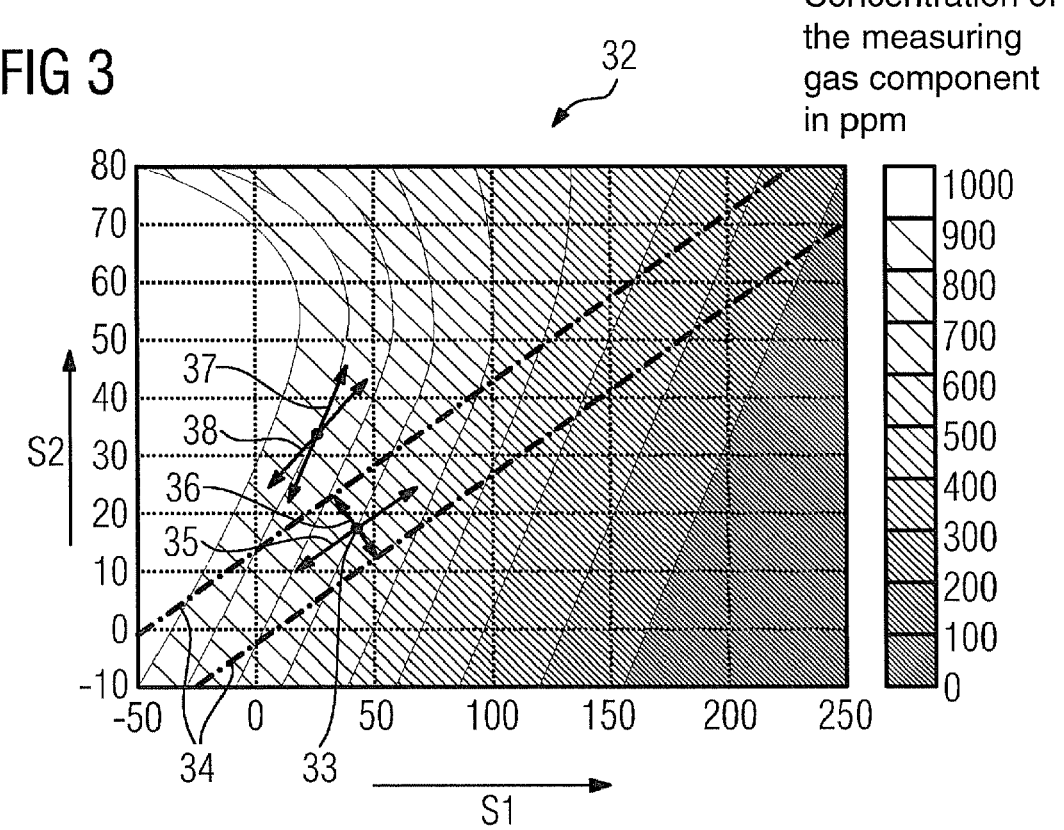
FIG. 3 shows an example of the calibration matrix.

FIG. 1 shows an NDIR gas analyzer 1 in single-beam design, comprising an infrared radiator 2 which produces test radiation 3. The test radiation 3 radiates through a sample cell 4 containing a gas mixture 5 with a measuring gas component whose concentration is to be determined. In the process the test radiation 3 is modulated by means of a modulator wheel (chopper) 6 arranged between the infrared radiator 2 and the sample cell 4. After radiating through the sample cell 4 the test radiation 3 falls onto a detector arrangement 7, comprising a first single-layer receiver 8 and an additional, downstream single-layer receiver 9. Each of the two single-layer receivers 8, 9 comprises a respective active detector chamber 10 and 11, located in the beam path 3 of the gas analyzer 1, and, outside of the beam path 3, a passive equalizing chamber 12 and 13, which are connected to each other by a connecting line 14 and 15 with a pressure- or flow-sensitive sensor 16 and 17 arranged therein. The sensors 16 and 17 produce signals S1 and S2 from which the concentration of the measuring gas component in the gas mixture 5 is determined in evaluating device 18 as measuring result M.

The NDIR gas analyzer 1' shown in FIG. 2 differs from that in FIG. 1 by a two-beam construction. The test radiation 3 produced by the infrared radiator 2 is divided by means of a beam splitter 19 (what is known as a Y-cell) into a measuring beam path through the sample cell 4, containing the gas mixture 5 with the measuring gas component, and a comparison beam path through a comparison cell 21 filled with a comparison gas 20. Downstream of the sample cell 4 and the comparison cell 21 the measuring beam path and the comparison beam path are brought together again by means of a radiation collector 22 and then arrive in the detector arrangement 7 already described with reference to FIG. 1.

The evaluating device 18 contains a calibration matrix 32 which is shown in detail in FIG. 3 and using which the mode of operation of the detector arrangement 7 will be described in more detail below.

Different transverse gas concentrations are successively introduced with different concentrations of measuring gas component into sample cell 4. A pair of values (2-tuples) 33 of signals S1 and S2 is measured for each available concentration, as is shown by way of example in the following table. The calibration matrix 32 is created from the recorded value pairs of signals S1 and S2 and the associated known concentration values of the measuring gas component, intermediate values being formed by interpolation of the recorded or known basic values. The calibration matrix 32 can also be in the form of a mathematical function that describes it and the associated function parameter can be stored in the evaluating device 18, for example using polynomials. A reduced series of measurements according to the table may be sufficient to create the calibration matrix 32.

| Measuring gas component in ppm | Transverse gas component in ppm | S1 | S2 |
|---|---|---|---|
| 0 (zero test gas) | 0 | … | … |
| 0 | 5000 | … | … |
| 0 | 10000 | … | … |
| 0 | 15000 | … | … |
| 500 (mean concentration) | 0 | … | … |
| 500 | 5000 | … | … |
| 500 | 10000 | … | … |
| 500 | 15000 | … | … |
| 1000 (final value gas) | 0 | … | … |
| 1000 | 5000 | … | … |
| 1000 | 10000 | … | … |
| 1000 | 15000 | … | … |

For real measuring situations the transverse gases and the expected deviations in their concentrations (for example minimum 5000 ppm to maximum 15000 ppm) are usually known, so a corridor 34 can be established in the calibration matrix 32, within which the n-tuples 33 dependent on the concentrations of the measuring gas component and the known transverse gases will normally lie. With changeable concentrations of the measuring gas component the n-tuples 33 move in the direction designated 35 and with the expected changeable concentrations of the transverse gases in the direction designated 36. These directions of movement 35 and 36 can be overlaid by other directions of movement resulting from variations in additional measuring and/or device-specific parameters, for example the power of the infrared radiator 2 or contamination of the sample cell 4. If an n-tuple 33 moves out of the corridor 34, then this points toward a disruption. As, compared with the further parameters, the effect of the known transverse gases is negligible outside of the corridor 34, the respective parameter, for example change in radiant power or unknown transverse gas, can be inferred from the additional direction of movement 37 or 38 of the n-tuple.

To detect all errors or disruptions in the parts of the beam path (infrared radiator 2, beam splitter 19, radiation collector 22, detector arrangement 7) through which the measuring and comparison radiation pass together in the gas analyzer with the two-beam construction shown in FIG. 2, the radiation 3 is advantageously asymmetrically coupled into the measuring and comparison beam path, for example in the ratio 55% to 45%. As a result the advantage of the two-beam construction is reduced in relation to the fixed zero setting but, on the other hand, errors can be detected which it would not otherwise be possible to identify.

Figure 4:
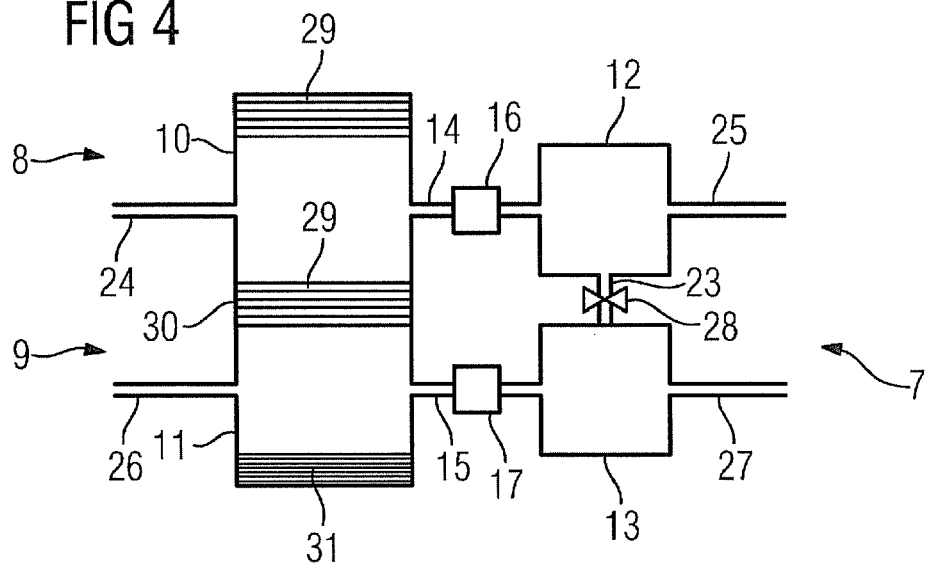
FIG. 4 shows an example of the inventive detector arrangement.

Finally, FIG. 4 shows an exemplary embodiment of the inventive detector arrangement 7 which allows its alternative use as a two-layer receiver, so different types of detector arrangement do not have to be produced for different applications. The equalizing chambers 12, 13 of the first and second single-layer receivers 8, 9 are connected to each other by a closable capillary 23. The capillary 23 is dimensioned such that it acts as a pneumatic low-pass filter and the changes in pressure caused by modulation of the radiation 3 in the single-layer receivers 8, 9 are not transmitted between the equalizing chambers 12, 13.

With inventive use of the detector arrangement 7 the capillary 23 is closed and the single-layer receivers 8, 9 are filled separately with different gases or different gas concentrations using gas ports 24, 25, 26, 27. Closure 28 of the capillary 23 can take place using an adjustable valve or, when producing the detector arrangement 7, by adhesive or by fusing the capillary 23.

When using the detector arrangement 7 as a two-layer detector the capillary 23 is open, so both halves 8, 9 of the two-layer detector can be filled with gas in a single filling step. If, owing to different leakage rates, the escape of gas from the two halves 8, 9 of the two-layer detector is different over a relatively long period, a pressure and concentration equalization occurs between the two halves 8, 9 of the two-layer detector via the capillary 23, whereby the measuring error is minimized. As the capillary 23 acts as a pneumatic low-pass filter the meteorological periodic changes in pressure are not transmitted between the two halves 8, 9 of the two-layer detector.

As FIG. 4 also shows, the active detector chambers 10, 11 comprise windows 29 to let in the radiation 3. Instead of an outlet window a mirror 31 can be provided to close the final detector chamber 11 in order to thus enlarge the optically effective length of the final detector chamber 11. However, a window may also be provided in order to arrange a further two-layer detector behind the first one.

The invention claimed is:

1. A detector arrangement for a non-dispersive infrared gas analyzer for detecting a measuring gas component in a gas mixture, comprising:
    a first single-layer receiver containing a measuring gas component or a gas spectrally overlaying the measuring gas component;
    a second single-layer receiver containing a transverse gas, a measuring gas component or a gas spectrally overlaying the measuring gas component; and
    an evaluating device for determining a concentration of the measuring gas component in the gas mixture from signals supplied from sensors of the first and second single-layer receivers,
    wherein the first and second single-layer receivers are located one behind the other in a beam path of the infrared gas analyzer,
    wherein the evaluating device includes a two-dimensional calibration matrix corresponding to a number of single-layer receivers,
    wherein signal values from the sensors obtained in the case of different known concentrations of the measuring gas component in the presence of different known transverse gas concentrations are stored in the evaluating device as two-tuples, and wherein the evaluating device is configured to determine the concentration of the measuring gas component when measuring unknown concentrations of the measuring gas component in the presence of unknown transverse gas concentrations by comparing the two-tuples of signal values obtained thereby with the two-tuples of signal values stored in the calibration matrix.

2. The detector arrangement as claimed in claim 1, wherein the detector arrangement comprises a plurality n of single-layer receivers containing a transverse gas, a measuring gas component or a gas spectrally overlaying the measuring gas component, wherein the evaluating device includes an n-dimensional calibration matrix corresponding to the plurality n of single-layer receivers, wherein the signal values from the sensors obtained in the case of different known concentrations of the measuring gas component in the presence of different known transverse gas concentrations are stored in the evaluating device as n-tuples, and wherein the evaluating device is configured to determine the concentration of the measuring gas component when measuring unknown concentrations of the measuring gas component in the presence of unknown transverse gas concentrations by comparing the n-tuples of signal values obtained thereby with the n-tuples of signal values stored in the calibration matrix.

3. The detector arrangement as claimed in claim 1, wherein the single-layer receivers each comprise an active detector chamber located in the beam path of the gas analyzer, and a passive equalizing chamber outside of the beam path, wherein the detector chamber and equalizing chamber are connected to each other by a connecting line with the sensor arranged therein.

4. The detector arrangement as claimed in claim 1, wherein the sensors are pressure- or flow-sensitive sensors.

5. The detector arrangement as claimed in claim 2, wherein the single-layer receivers each comprise an active detector chamber located in the beam path of the gas analyzer, and a passive equalizing chamber outside of the beam path, wherein the detector chamber and equalizing chamber are connected to each other by a connecting line with the sensor arranged therein.

6. The detector arrangement as claimed in claim 2, wherein the sensors are pressure- or flow-sensitive sensors.

7. The detector arrangement as claimed in claim 3, wherein for an alternative use as a two-layer receiver the equalizing chambers of the first and second single-layer receiver are connected to each other by a closable capillary.

8. The detector arrangement as claimed in claim 5, wherein for an alternative use as a two-layer receiver the equalizing chambers of the first and second single-layer receiver are connected to each other by a closable capillary.

9. A method for detecting a measuring gas component in a gas mixture, comprising:

providing a non-dispersive infrared gas analyzer;

providing a detector arrangement comprising a first single-layer receiver and at least one additional single-layer receiver, the first single-layer receiver containing a measuring gas component or a gas spectrally overlaying the measuring gas component and the at least one additional single-layer receiver containing a transverse gas, the measuring gas component or a gas spectrally overlaying the measuring gas component;

arranging the first and at least one additional single-layer receiver one behind the other in a beam path of the gas analyzer;

using an n-dimensional calibration matrix corresponding to the number n of single-layer receivers;

storing signal values from the sensors obtained in the case of different known concentrations of the measuring gas component in the presence of different known transverse gas concentrations in the n-dimensional calibration matrix as n-tuples;

measuring unknown concentrations of the measuring gas component in the presence of unknown transverse gas concentrations and obtaining signal values and n-tuples thereof; and comparing the n-tuples of the unknown concentrations of the measuring gas component with the n-tuples of signal values stored in the calibration matrix.

10. The method as claimed in claim 9, wherein the additional single-layer receiver is filled with a transverse gas or the measuring gas component or a gas which spectrally overlays the gas to be measured, and wherein the concentration of the respective transverse gas component is determined when measuring unknown concentrations of the measuring gas component in the presence of unknown transverse gas concentrations by comparing the n-tuples of signal values obtained thereby with the n-tuples of signal values stored in the calibration matrix.

11. The method as claimed in claim 9, further comprising:

establishing a corridor in the calibration matrix, starting from expected transverse gas concentrations and their deviations, and signaling an error when measuring unknown concentrations of the measuring gas component in the presence of the expected transverse gas concentration and when the n-tuples of signal values obtained thereby lie outside of the corridor.

12. The method as claimed in claim 10, further comprising:

establishing a corridor in the calibration matrix, starting from expected transverse gas concentrations and their deviations, and signaling an error when measuring unknown concentrations of the measuring gas component in the presence of the expected transverse gas concentration and when the n-tuples of signal values obtained thereby lie outside of the corridor.

13. The method as claimed in claim 9, wherein, when measuring parameters and/or device-specific parameters are kept constant, an additional parameter of this kind is varied and a direction in which the n-tuples of the signal values obtained vary within the calibration matrix is determined.

14. The method as claimed in claim 10, wherein, when measuring parameters and/or device-specific parameters are kept constant, an additional parameter of this kind is varied and a direction in which the n-tuples of the signal values obtained vary within the calibration matrix is determined.

15. The method as claimed in claim 11, wherein, when measuring parameters and/or device-specific parameters are kept constant, an additional parameter of this kind is varied and a direction in which the n-tuples of the signal values obtained vary within the calibration matrix is determined.

16. The method as claimed in claim 12, wherein, when measuring unknown concentrations of the measuring gas component in case of a movement of the n-tuples of signal values obtained thereby from the corridor, the measuring parameter and/or device-specific parameter associated with the movement direction of the n-tuples is determined, the effect of its error being reduced.

17. The method as claimed in claim 13, wherein, when measuring unknown concentrations of the measuring gas component in case of a movement of the n-tuples of signal values obtained thereby from the corridor, the measuring parameter and/or device-specific parameter associated with the movement direction of the n-tuples is determined, the effect of its error being reduced.

* * * * *